United States Patent [19]
Kost et al.

[11] Patent Number: 5,631,456
[45] Date of Patent: May 20, 1997

[54] REFLECTION CONTROL APPARATUS

[75] Inventors: Karen L. Kost; William J. Fry; Timothy J. Lock, all of Ann Arbor; Michael S. Davis, South Lyon, all of Mich.

[73] Assignee: Lynn Ltd., Ann Arbor, Mich.

[21] Appl. No.: 397,777

[22] Filed: Mar. 3, 1995

Related U.S. Application Data

[63] Continuation-in-part of Ser. No. 203,546, Mar. 1, 1994, Pat. No. 5,554,841.

[51] Int. Cl.⁶ ..................................................... G06K 7/10
[52] U.S. Cl. ............................................ 235/462; 235/454
[58] Field of Search ................................... 235/462, 472, 235/469, 454, 463, 467, 466, 455, 470

[56] References Cited

U.S. PATENT DOCUMENTS

| | | | |
|---|---|---|---|
| 2,292,044 | 8/1942 | Bucky | 240/2 |
| 2,541,016 | 2/1951 | Allen | 95/14 |
| 2,642,518 | 6/1953 | Bates | 240/2 |
| 2,727,427 | 12/1955 | Jenkins | 88/16 |
| 2,763,772 | 9/1956 | Hine | 240/1.3 |
| 2,792,740 | 5/1957 | Haynes | 359/637 |
| 2,926,559 | 3/1960 | Oppenheimer | 359/629 |
| 3,034,406 | 5/1962 | McKenzie | 88/82 |
| 3,198,097 | 8/1965 | Hine | 95/11 |
| 3,784,288 | 1/1974 | Toy | 350/302 |
| 3,811,770 | 5/1974 | Baus, Jr. | 355/67 |
| 3,944,336 | 3/1976 | Carr, Jr. | 359/629 |
| 3,984,157 | 10/1976 | LeVantine | 359/614 |
| 3,985,425 | 10/1976 | Clapp | 350/147 |
| 4,034,387 | 7/1977 | Ohtaki | 354/126 |
| 4,185,902 | 1/1980 | Plaot | 359/614 |
| 4,561,722 | 12/1985 | Smetana | 350/171 |
| 4,666,292 | 5/1987 | Imamura | 355/67 |
| 4,712,889 | 12/1987 | Schindl | 359/389 |
| 4,791,534 | 12/1988 | Lindberg | 359/629 |
| 4,854,688 | 8/1989 | Hayford et al. | 359/433 |
| 4,877,326 | 10/1989 | Chadwick et al. | 359/389 |
| 4,924,199 | 5/1990 | Hashimoto et al. | 235/494 |
| 4,991,947 | 2/1991 | Sander et al. | 359/389 |
| 5,011,265 | 4/1991 | Tamamura et al. | 350/173 |
| 5,053,612 | 10/1991 | Pielemeier et al. | 235/462 |
| 5,187,611 | 2/1993 | White et al. | 359/599 |
| 5,233,170 | 8/1993 | Matlitsky et al. | 235/454 X |
| 5,313,373 | 5/1994 | Bjorner et al. | 362/19 |
| 5,374,813 | 12/1994 | Shipp | 235/375 |
| 5,430,285 | 7/1995 | Karpen et al. | 235/472 |

FOREIGN PATENT DOCUMENTS 768394  2/1957  France ........................... 235/462

*Primary Examiner*—Donald T. Hajec
*Assistant Examiner*—Thien Minh Le
*Attorney, Agent, or Firm*—Gifford, Krass, Groh, Sprinkle, Patmore, Anderson & Citkowski

[57] ABSTRACT

A device for controlling reflections off of and information-bearing surface is especially suitable for use in conjunction with shiny, curved surfaces containing machine-readable markings. The device includes a chamber having an interior wall and entrance and exit apertures, the entrance aperture being associated with receiving an image of the surface, and the exit aperture being associated with delivering the image of the surface to image sensing means. As the delivered image of the surface may potentially include reflections of the interior wall and exit aperture, means are provided for equalizing these reflections to minimize problems associated with sensing the image of the surface and decoding any information present. The interior of the chamber is preferably uniformly illuminated to at least control the reflections associated therewith, and to equalize reflections associated with the exit aperture, a beam splitter supported and illuminated, preferrably utilizing a source of illumination and a transluscent panel supported between the source and the beam splitter. The illumination sources associated with the chamber interior and beam-splitter may be independently adjustable, and infrared radiation is preferrably used to obscure surface roughening.

15 Claims, 2 Drawing Sheets

REFLECTION CONTROL APPARATUS

REFERENCE TO RELATED APPLICATIONS

This application is a continuation-in-part of U. S. patent application Ser. No. 08/203,546, filed Mar. 1, 1994 now U. S. Pat. No. 5,554,841.

FIELD OF THE INVENTION

The present invention relates generally to object reflective surfaces, and means for controlling reflections therefrom. One application involves the decoding of machine-readable symbology applied to, or etched in, such surfaces.

BACKGROUND OF THE INVENTION

Machine-readable codes are being used on an increasing variety of articles for the purposes of organizing tracking such articles, discouraging theft, and so forth. For example, machine-readable codes are now in common use on grocery store items, identification cards, waybills, and other applications. The parent to this application, Ser. No. 08/203,546, incorporated herein in its entirety by reference, discloses methods and apparatus for marking articles having hard, shiny, and even curved surfaces, with a machine-readable code, and systems and techniques enabling such codes to be reliably interpreted despite conditions hostile to reliable imaging. Curved, shiny surfaces, in particular, present extreme challenges with regard to machine readability. On one hand, imaging of the article surface in the vicinity of an encoded marking typically benefits from controlled illumination, but even when steps are taken to ensure that such illumination is uniformly applied, curved, specular surfaces in particular tend to produce hot spots at the detector apparatus, causing problems associated with simultaneous control over critical imaging parameters such as brightness and contrast.

A solution to this problem, disclosed in the above-referenced parent application, takes the form of a controlled environment for observing encoded marks made on such surfaces. Broadly, the approach involves indirect lighting of a surface or volume to be intentionally reflected from the article surface and onto the detector, thus enhancing visual differentiation between areas associated with machine-readable symbology, and areas of the article surrounding such symbology. Thus, rather than concentrating on uniformly illuminating the article itself, attention is instead turned to illuminating a surface reflected by the article in such a way that the reflections are of constant value and more conducive to normalization. To successfully carry out this approach, a plurality of illumination sources are supported with respect to a volume having an interior surface, causing reflections from the information-bearing surface to "see" portions of this illuminated interior volume, resulting in controlled reflections with respect to a detector mechanism. This apparatus has proved successful with regard to the decoding of machine-readable symbology associated with difficult surfaces, including hard, shiny and curved surfaces associated with metallic objects, including surgical instruments, and the like. Despite the marked improvement in the readability of such symbology, however, improvements to the basic principles introduced above have been discovered, and are disclosed and claimed herein.

SUMMARY OF THE INVENTION

The present invention is directed toward a device for controlling reflections off of an information-bearing surface. The invention is especially suitable for use in conjunction with shiny, curved surfaces containing machine-readable markings. Broadly, the apparatus includes a chamber having an interior wall and entrance and exit apertures, the entrance aperture being associated with receiving an image of the surface, and the exit aperture being associated with delivering the image of the surface to image sensing means. As the delivered image of the surface may potentially include reflections of the interior wall and exit aperture, means are provided for equalizing these reflections to minimize problems associated with sensing the image of the surface and decoding any information present.

In the preferred embodiment, means are provided for uniformly illuminating the chamber to at least control the reflections associated with the interior of the chamber, including one or more light sources configured so that no radiation from any source impinges upon the information-bearing surface directly. To equalize reflections associated with the exit aperture to those associated with the interior of the chamber the preferred embodiment further includes a beam splitter supported in an optical path between the exit aperture and the image sensing means, the beam splitter having a first surface facing generally toward the exit aperture and a second surface facing generally toward the image sensing means. The first surface of the beam splitter is then uniformly illuminated to be in visible agreement with the uniformly illuminated chamber interior using a source of illumination and a translucent panel supported between the source and the first surface of the beam splitter. With further regard to the preferred embodiment, the illumination sources associated with the chamber interior and beam-splitter first surface are independently adjustable, and infrared radiation is used to obscure spurious, sub-wavelength variations which may be present in the information-bearing surface.

DETAILED DESCRIPTION OF THE PREFERRED EMBODIMENTS

Figure 1:
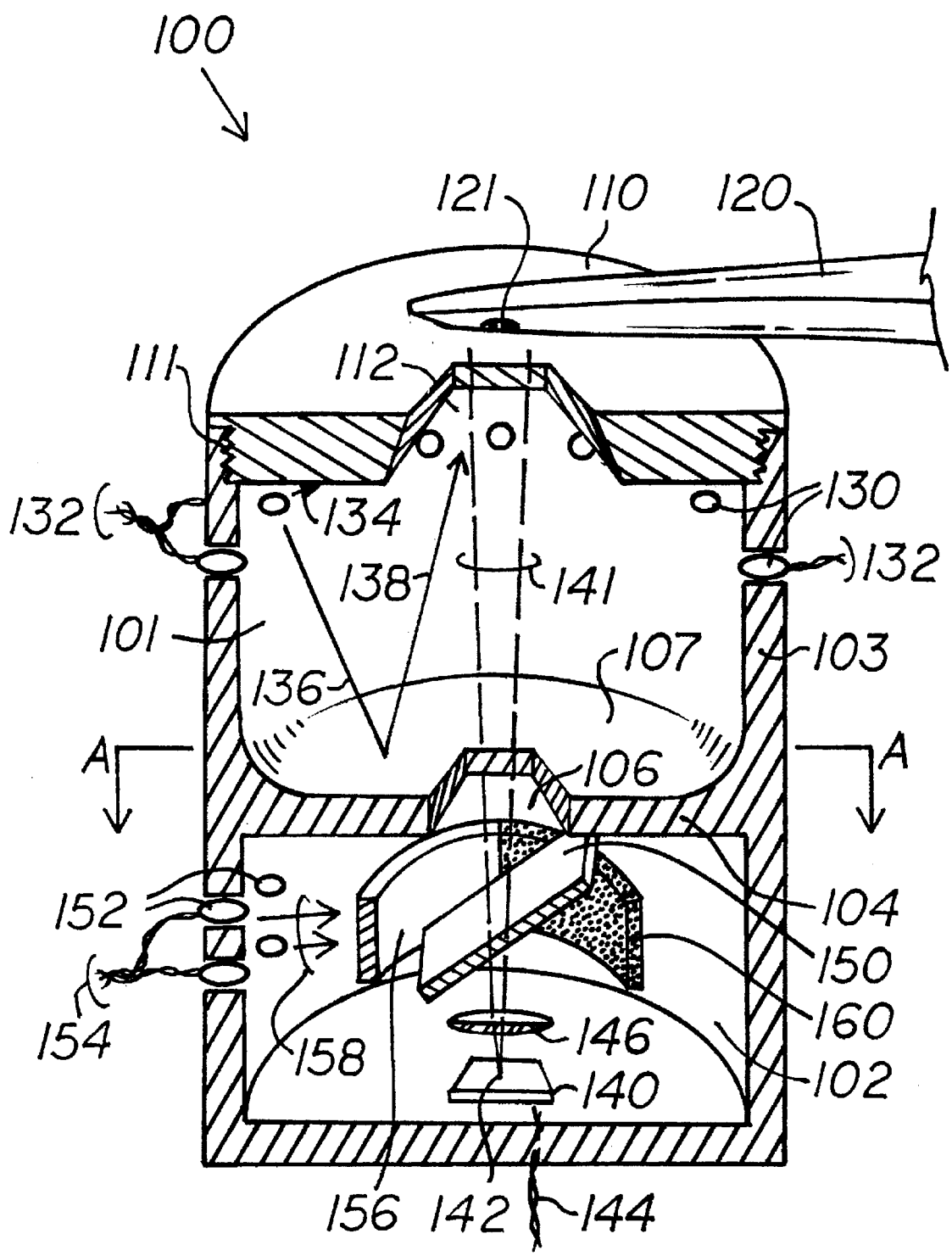
FIG. 1 is a cross-section of an apparatus formed in accordance with the invention, seen from an oblique perspective.

Shown generally at 100 is an apparatus formed according to the invention, in this case a device for observing the surface, of an article 120 having machine-readable symbology 121 associated therewith. This symbology is to be accurately focused onto image sensor 140 in the area 142, and converted to representative electrical signals and transmitted over signal paths 144 to a computer and display apparatus for analysis and interpretation. In the event that symbology 121 is placed on an article 120 having a shiny or curved surface, or a combination of such surfaces, upon illumination of the surface area in the vicinity of the symbology 121, undesirable reflections visible in the surface of article 120.

These reflections will also be focused by lens 146 onto the image sensor 140, potentially causing problems in distinguishing the markings comprising symbology 121 and areas surrounding, and perhaps within, the surface area containing the symbology. Typically these unwanted reflections from the article create hot spots on the detector 140, leading to problems associated with the simultaneous control over brightness and contrast, making interpretation of the symbology 121 technically challenging.

The device 100 controls reflections associated with surfaces of the article 120 seen by the imager 140, so that the markings associated therewith are more distinguishable with respect to non-information bearing surfaces of the article. It should be noted that the apparatus has uses beyond the observation and interpretation of machine-readable codes, and may be extended to more general surface analysis techniques, for example, where unwanted or foreign particles or coatings are to be identified, particularly on smooth or shiny and curved surfaces. It should also be recognized that the invention should be interpreted in light of the broad principles disclosed herein, and not limited to the use of particular components or geometries. For example, while infrared radiation is preferably used in this application, other wavelengths may alternatively be used. Also, while a two-dimensional, solid-state imager is preferably employed, other options are available, including scanning techniques. Finally, the geometries associated with the figures should not necessarily be taken as representative of the only possible configuration, and other dimensions are possible, including off-axis illumination and detection techniques.

Broadly, the device 100 consists of an upper chamber 101 having the first aperture 112 inputting a view of article 120 having symbology 123, and a second aperture 106, preferably in opposed, facing relation to first aperture 112, the aperture 106 being associated with delivering an image of the article and symbology to detector 140. In the preferred embodiment, the chambers 101 and 102 are defined in an outer shell casing 103, preferably constructed of a rigid, workable material such as stainless steel. The various panels and spacers associated with the enclosure overall may be constructed using dismantleable fittings, such as threaded connection 111, though, for areas not requiring maintenance, weldment and other more permanent techniques may alternatively be used for construction.

The embodiment shown in FIG. 1 may either be used in upright fashion, as depicted, or may be incorporated into a portable, hand-held type of instrument, in which case article 120 may be lying on a surface with symbology 121 facing upwardly, and with the device 100 being inverted from the orientation shown in FIG. 1 and held over the article 120 with aperture 112 facing downwardly.

Broadly, devices and geometries associated with the first chamber 101 are designed to provide the majority of uniform reflectivity off the surface of article 120, with the exception being reflections associated with the aperture 106, which will otherwise appear reflected off article 120, though in distorted form with the presence of curved surfaces. Thus, the function of devices and geometries associated with chamber 102 are to cause reflections associated with the aperture 106 to appear as close to identical as possible with all other reflections visibly present from the surface of article 120, including those associated with the chamber 101.

To provide for uniform reflections in conjunction with the chamber 101, the plurality of illumination sources 130 are used, and are preferably spaced apart annularly as shown, protruding through the wall of the chamber 101 enabling the connectors 132 to make operative connection to a power supply. The sources of illumination 130 are supported such that illumination therefrom cannot strike the surface of the article directly, as shown by ray 134 but instead, illumination from the sources must necessarily be reflected by an inner surface of the chamber 101, such as bottom surface 107, with the reflected ray being shown with lines 136 and 138. This bottom surface 101, and the inner side walls comprising the chamber 101 are preferably of a uniform value, so as to control the reflection of such surfaces in the article 120. Preferably, some sort of uniform coding such as white paint is used, though other alternatives are available, including other colors, surface treatments, and so forth. Also, the lower section of chamber 101 may be curved, as shown with numerical reference 139, or, indeed, the bottom of chamber 101 may be hemispherical in shape.

Without the elements in the lower chamber 102, the reflection of a surface of article 120, depicted with lines 141, would be acceptably uniform with respect to surfaces within chamber 101, but aperture 106 and a reflection of the focusing element 146 and defector 140 would no doubt additionally be seen in reflections from article 120, depending upon the circumstances. Thus, the elements shown in FIG. 1 below the aperture 106 are used to "knock out" reflections associated with the aperture itself and the elements contained within chamber 102, and further, preferably to equalize the reflected value associated between the chamber 101, aperture 106 and the elements therebelow so that the machine-readable symbology 121 is viewed in conjunction with a consistent surrounding.

To facilitate this equalization, a beam-splitter 150 is supported in the optical path between symbology 121 and detector 140, and is placed at an angle of preferably 45 degrees, as shown. A separate set of illumination sources 152, having power connections 154, is used to illuminate the wall of a translucent element 156, with the rays of illumination being shown at 158. This element 156 is preferably of a cylindrical design, having a backwall portion 160 being made dark and opaque material. Preferably, all interior walls of the lower chamber 102 are likewise made intentionally darkened and non-reflective with exception of the translucent panel area 156. With such an arrangement, illumination from source 158 causes the translucent portion 156 of this cylindrical element to glow, and this glow is reflected off of the upper surface of beam-splitter 150 and projected upward and through apertures 106 and 112, and onto the surface of the article 120 which contains the machine-readable symbology 121. This reflected glow then bounces off of the article and back down through the aperture 112 and 106, and at least a portion continues to travel through beam-splitter 150 and focused by elements 146 onto detector 140. With the power to illumination sources 152 and 132 being independently controlled, their glow associated with surface 156 may be increased or decreased, in accordance with other aspects of the configuration, including transmission characteristics of beam splitter 150, and so forth, to ensure that, now, the final reflection in need of compensation, that of aperture 106 and those elements therebelow, is made to equalize with all reflections off of the interior walls of chamber 101, so that now symbology 121 may be that much more free of uncontrolled and undesirable reflectance.

Figure 2:
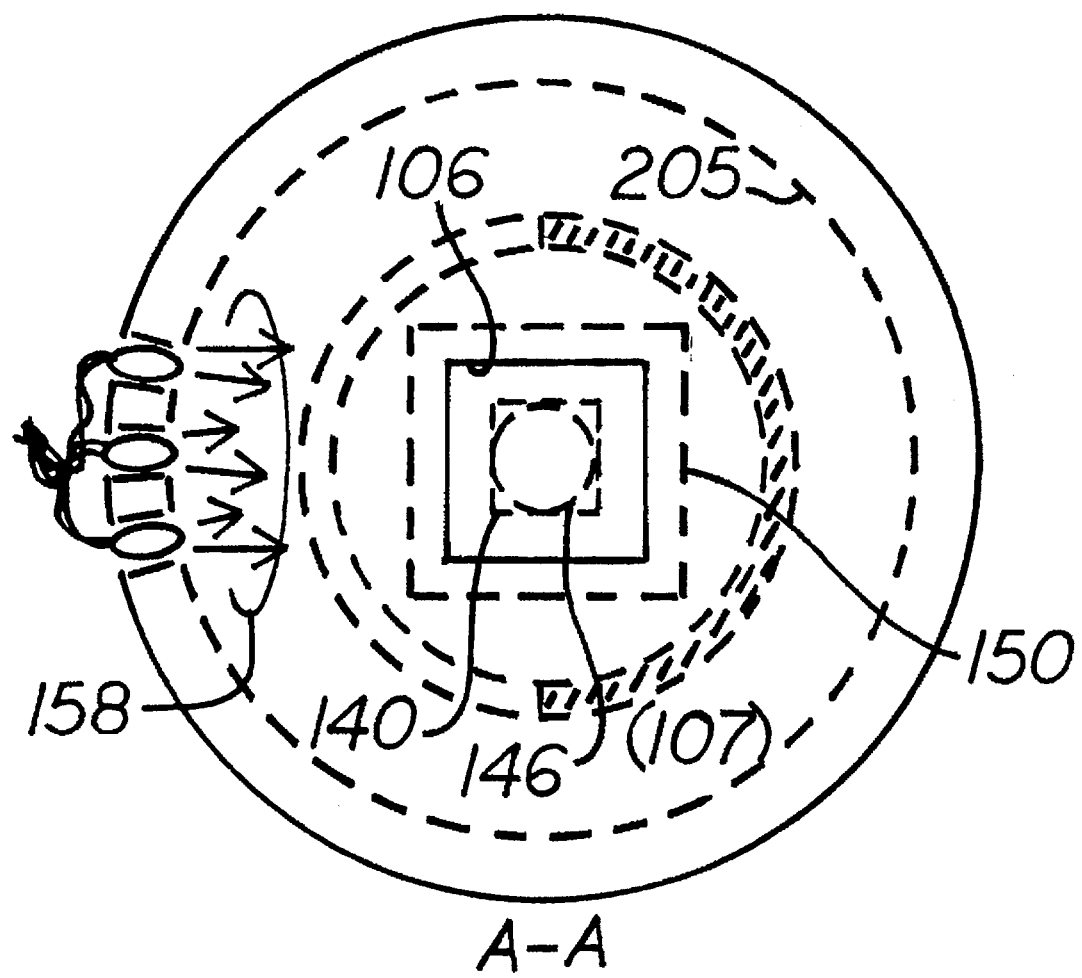
FIG. 2 is a top down view taken with respect to Section A—A in FIG. 1.

This compensation between interior surface of chamber 101 and reflections from beam-splitter 150 may perhaps be better understood with reference to FIG. 2, which shows a top-down view taken along Section A—A of FIG. 1. As seen from this view, the outer wall of the casing 103 is shown as a circular solid line, with the circular dashed line 205 being indicative of the inner wall of the lower chamber 102. The image sensor 140 is shown here in broken-line form as a square, and lens element 146 is shown with broken lines as a circle. The outer edge of beam-splitter 150 is shown as a square, in broke form, with the outer edges of the beam-splitter extending in all directions peripherally with respect to the aperture 106. The elements surrounding the beam-splitter having the translucent portion 156 and opaque portion 160 is clearly seen in this view as cylindrical in shape, though it must be pointed out that other shapes may alternatively De used for this purpose. Indeed, panels 156 and 160 are absolutely necessary, in the event that it is otherwise possible to cause a uniformly controllable glow to appear reflected off of the surface of beam splitter 150 and toward the article under inspection.

In FIG. 2, only two shapes are shown in solid-line form, these being the outer circular shape of the shell casing itself, and the smaller square representative of aperture 106. Essentially, the goal of this invention is to equalize the reflections associated with these two geometries, ideally, to completely "knock out" the square representative of aperture 106, so that only a single, homogeneous surface of constant value is reflected off of the article containing the machine-readable symbology, facilitating a fast and accurate interpretation of the code contained therein.

In operation, the article 120 is placed proximate to the aperture 112 as shown, or, alternatively, as previously mentioned, the apparatus of the invention is brought approximately to a stationary article. In one embodiment, both sources of illumination 130 associated with the chamber 101 and 152 associated with the chamber 102 are left "ON" for use with multiple encoded articles, these sources having previously been adjusted to provide the type of compensation previously described above. It should be noted that "ON" can be taken to mean continuously powered or, alternatively, pulsed with a duty cycle appropriate to the application. In an alternative embodiment, the article 120 may be sensed by instrument, with the sources of illumination then being activated or pulsed in accordance with such sensing. This sensing may be carried out either with the apparatus as shown, by detecting changes in the field of view of image sensor 140, or, alternatively, using other, known, sensing techniques (not shown). As a further alternative, the activation of sources of illumination 130 and/or 152 may be timed in conjunction with the reading out of image sensor 140, in the event that such timing improves readability, symbology, saves of power advantages or provides other advantages.

Having thus described the invention, I claim:

1. A device for controlling reflections off of an information-bearing surface, comprising:
    a chamber having a first opening through which to view the surface and a second opening to output an image of the surface, the image potentially including reflections associated with the interior of the chamber and the second opening,
    means for uniformly illuminating the chamber to at least control the reflections associated with the interior of the chamber;
    image sensing means supported outside the second opening to receive the image of the surface; and
    means for equalizing the reflections associated with the second opening with those associated with the interior of the chamber, including:
        a beam splitter supported in an optical path between the second opening and the image sensing means, the beam splitter having a first surface facing generally toward the second opening and a second surface facing generally toward the image sensing means; and
        means for controllably illuminating the first surface of the beam splitter.

2. The device of claim 1, wherein the means for controllably illuminating the first surface of the beam splitter includes:
    a source of variable-intensity illumination; and
    a translucent panel supported between the source of variable-intensity illumination and the first surface of the beam splitter.

3. The device of claim 1, wherein the means for equalizing the reflections associated with the second opening with those associated with the interior of the chamber further includes means for equalizing the illumination of the interior of the chamber and the illumination of the first surface of the beam splitter.

4. The device of claim 1, wherein the means for illuminating the chamber utilizes infrared radiation.

5. The device of claim 1, wherein the image sensing means includes:
    means for focussing the outputted image of the surface; and
    a two-dimensional solid-state image sensor.

6. The device of claim 1, wherein the information-bearing surface includes a shiny, curved surface.

7. A device for controlling reflections off the surface of an article under observation, comprising:
    a chamber having first and second apertures opening into an interior volume, the first aperture being associated with inputting a view of a surface area of an article being observed, the second aperture being associated with outputting an image of the area being viewed, and the interior volume including a surface adapted to provide a visually consistent reflection at least with respect to the interior volume;
    a two-dimensional image sensor supported outside the chamber and in an optical path relative to the second aperture;
    means for focussing the outputted image of the area being viewed onto the image sensor;
    a beam splitter supported in the optical path, the beam splitter having a first surface facing generally toward the second aperture and a second surface facing generally toward the two-dimensional image sensor; and
    means for illuminating the first surface of the beam splitter so that an image of the reflection of the first surface as seen in the article passes through the beam splitter and is visually consistent with the reflection associated with the interior volume.

8. The device of claim 7, wherein the surface of the article under observation, first aperture, second aperture, image sensor, and means for focussing are aligned along an optical axis, and wherein the beam splitter is supported at a point along the axis at an angle, enabling off-axis illumination of the first surface of the beam splitter.

9. The device of claim 7, wherein the means for illuminating the first surface of the beam splitter includes a source of illumination and a transluscent panel disposed between the source of illumination and the first surface of the beam splitter.

10. The device of claim 7, further including means for illuminating the interior volume of the chamber to provide a visually consistent reflection with respect thereto.

11. The device of claim 10, including infrared means for illuminating the interior volume of the chamber and the first surface of the beam splitter.

12. The device of claim 10, including means for independently adjusting the illumination of the interior volume of the chamber and the first surface of the beam splitter.

13. The device of claim 11, wherein the means for illuminating the interior volume of the chamber includes a plurality of illumination sources spaced apart along the interior surface of the chamber, the positioning of the sources being such that the surface of the article is not illuminated directly by such sources, but rather, by light reflected off the interior volume surface adapted to provide a visually consistent reflection at least with respect to the interior volume.

14. The device of claim 7, the surface of the article being specular.

15. The device of claim 14, the surface of the article being curved.

* * * * *

UNITED STATES PATENT AND TRADEMARK OFFICE
CERTIFICATE OF CORRECTION

PATENT NO.   : 5,631,456
DATED        : May 20, 1997
INVENTOR(S)  : Karen L. Kost et al It is certified that error appears in the above-indentified patent and that said Letters Patent is hereby corrected as shown below:

Column 1, line 10:   After "object" insert --illumination, and, in particular, to the observation of--.

Column 2, line 48:   After "surface" delete the comma (,).

Column 3, line 24:   Replace "123" with --121--.

Column 3, line 66:   Replace "101, and" with --107 and--.

Column 4, line 12:   Replace "defector" with --detector--.

Column 5, line 2:    Replace "De" with --be--.

Column 4, line 63:   Replace "broke" with --broken line--.

Signed and Sealed this

Twenty-third Day of December, 1997

Attest:

BRUCE LEHMAN

Attesting Officer

Commissioner of Patents and Trademarks